(12) United States Patent
Kruger et al.

(10) Patent No.: US 12,390,280 B2
(45) Date of Patent: *Aug. 19, 2025

(54) DEVICE AND METHOD FOR CONNECTING A MEDICAL INSTRUMENT TO A POSITION-DETECTING SYSTEM

(71) Applicant: INTERSECT ENT GMBH, Hennigsdorf (DE)

(72) Inventors: Timo Kruger, Berlin (DE); Dirk Mucha, Berlin (DE)

(73) Assignee: FIAGON GMBH, Hennigsdorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/903,381

(22) PCT Filed: Jul. 14, 2014

(86) PCT No.: PCT/EP2014/065030
§ 371 (c)(1),
(2) Date: Jan. 7, 2016

(87) PCT Pub. No.: WO2015/007681
PCT Pub. Date: Jan. 22, 2015

(65) Prior Publication Data
US 2016/0143700 A1 May 26, 2016

(30) Foreign Application Priority Data
Jul. 17, 2013 (DE) .......................... 102013214067.3

(51) Int. Cl.
*A61B 34/20* (2016.01)
*A61B 17/00* (2006.01)
*A61B 90/00* (2016.01)

(52) U.S. Cl.
CPC .... *A61B 34/20* (2016.02); *A61B 2017/00477* (2013.01); *A61B 2017/00725* (2013.01);
(Continued)

(58) Field of Classification Search
CPC ............ A61B 34/20; A61B 2034/2051; A61B 2034/2068; A61B 2034/2072;
(Continued)

(56) References Cited

U.S. PATENT DOCUMENTS

| 4,905,698 A | 3/1990 | Strohl, Jr. et al. |
| 5,554,155 A | 9/1996 | Awh et al. |

(Continued)

FOREIGN PATENT DOCUMENTS

| DE | 19641720 A1 | 4/1998 |
| DE | 19944981 A1 | 4/2001 |

(Continued)

OTHER PUBLICATIONS

Anonymous, Change System/Upgrade order 1110000092: Overview, Mar. 14, 2008, 1 page.

(Continued)

*Primary Examiner* — Joel Lamprecht
(74) *Attorney, Agent, or Firm* — Nancy C. Wilker (57) ABSTRACT

The invention relates to a device for connecting a medical instrument to a position-detecting system, the device having a localization element. The medical instrument has an instrument shaft, an instrument tip and an operating point. At least one localization element for determining position information for the device within a coordinate system of the position-detecting system can be provided on the device, the device having at least one retaining means for attaching the localization element to the medical instrument.

14 Claims, 3 Drawing Sheets

(52) U.S. Cl.
CPC ........... *A61B 2034/2051* (2016.02); *A61B 2034/2068* (2016.02); *A61B 2034/2072* (2016.02); *A61B 2090/3983* (2016.02)

(58) Field of Classification Search
CPC .. A61B 2090/3983; A61B 2017/00477; A61B 2017/00725
See application file for complete search history.

(56) References Cited

U.S. PATENT DOCUMENTS

| | | | |
|---|---|---|---|
| 5,586,989 | A | 12/1996 | Bray, Jr. |
| 5,840,024 | A | 11/1998 | Taniguchi et al. |
| 5,944,023 | A | 8/1999 | Johnson et al. |
| 5,964,759 | A | 10/1999 | Yamanashi et al. |
| 5,971,997 | A * | 10/1999 | Guthrie ............ A61B 90/11 606/130 |
| 6,011,987 | A | 1/2000 | Barnett |
| 6,052,610 | A | 4/2000 | Koch |
| 6,161,032 | A | 12/2000 | Acker |
| 6,235,038 | B1 | 5/2001 | Hunter et al. |
| 6,248,074 | B1 | 6/2001 | Ohno et al. |
| 6,301,495 | B1 | 10/2001 | Gueziec et al. |
| 6,347,460 | B1 * | 2/2002 | Forrer ............ A61B 90/10 128/920 |
| 6,369,564 | B1 | 4/2002 | Khalfin |
| 6,370,420 | B1 | 4/2002 | Kraft |
| 6,432,041 | B1 | 8/2002 | Taniguchi et al. |
| 6,611,141 | B1 | 8/2003 | Schulz et al. |
| 6,618,612 | B1 | 9/2003 | Acker et al. |
| 6,661,571 | B1 | 12/2003 | Shioda et al. |
| 6,690,960 | B2 | 2/2004 | Chen et al. |
| 7,043,961 | B2 * | 5/2006 | Pandey ............ A61B 90/36 73/1.75 |
| 7,346,417 | B2 | 3/2008 | Luth et al. |
| 7,474,327 | B2 | 1/2009 | Davidson et al. |
| 7,491,198 | B2 | 2/2009 | Kockro |
| 8,067,726 | B2 * | 11/2011 | Groszmann ............ A61B 90/36 250/252.1 |
| 8,207,863 | B2 | 6/2012 | Neubauer et al. |
| 9,208,561 | B2 | 12/2015 | Kruger et al. |
| 9,333,047 | B2 | 5/2016 | Mucha |
| 9,410,802 | B2 | 8/2016 | Mucha et al. |
| 9,471,850 | B2 | 10/2016 | Krueger et al. |
| 9,641,808 | B2 | 5/2017 | Rose et al. |
| 10,022,525 | B2 | 7/2018 | Hanson et al. |
| 10,238,846 | B2 | 3/2019 | Ressemann et al. |
| 10,362,966 | B2 | 7/2019 | Kruger et al. |
| 10,368,851 | B2 | 8/2019 | Tuma et al. |
| 10,398,512 | B2 | 9/2019 | Mucha |
| 10,512,522 | B2 | 12/2019 | Verard et al. |
| 10,568,713 | B2 | 2/2020 | Kruger et al. |
| 11,065,061 | B2 | 7/2021 | Makower |
| 11,109,915 | B2 | 9/2021 | Mucha |
| 11,123,144 | B2 | 9/2021 | Bustan et al. |
| 11,337,661 | B2 | 5/2022 | Timo et al. |
| 11,357,574 | B2 | 6/2022 | Timo et al. |
| 2001/0021806 | A1 | 9/2001 | Gueziec et al. |
| 2003/0040670 | A1 | 2/2003 | Govari |
| 2003/0059097 | A1 | 3/2003 | Abovitz et al. |
| 2003/0066538 | A1 | 4/2003 | Martinelli et al. |
| 2003/0069588 | A1 | 4/2003 | Vilsmeier et al. |
| 2003/0209096 | A1 * | 11/2003 | Pandey ............ A61B 90/36 73/865.9 |
| 2003/0229279 | A1 | 12/2003 | Amstutz et al. |
| 2003/0231793 | A1 | 12/2003 | Crampton |
| 2004/0019274 | A1 | 1/2004 | Galloway, Jr. et al. |
| 2004/0024309 | A1 | 2/2004 | Ferre et al. |
| 2004/0054489 | A1 * | 3/2004 | Moctezuma De La Barrera ........ G16Z 99/00 702/105 |
| 2004/0073279 | A1 | 4/2004 | Malackowski et al. |
| 2004/0082849 | A1 | 4/2004 | Schweikard |
| 2004/0143183 | A1 | 7/2004 | Toyoda et al. |
| 2004/0169673 | A1 | 9/2004 | Crampe et al. |
| 2004/0199072 | A1 | 10/2004 | Sprouse et al. |
| 2004/0230199 | A1 | 11/2004 | Jansen et al. |
| 2004/0263535 | A1 | 12/2004 | Birkenbach et al. |
| 2005/0020909 | A1 | 1/2005 | Moctezuma De La Barrera et al. |
| 2005/0024043 | A1 | 2/2005 | Govari |
| 2005/0054895 | A1 | 3/2005 | Hoeg et al. |
| 2005/0085717 | A1 | 4/2005 | Shahidi |
| 2005/0085720 | A1 | 4/2005 | Jascob et al. |
| 2005/0101966 | A1 | 5/2005 | Lavallee |
| 2005/0107687 | A1 | 5/2005 | Anderson |
| 2005/0119639 | A1 | 6/2005 | McCombs et al. |
| 2005/0149050 | A1 | 7/2005 | Stifter et al. |
| 2005/0187562 | A1 * | 8/2005 | Grimm ............ A61F 2/4603 606/130 |
| 2005/0215854 | A1 | 9/2005 | Ozaki et al. |
| 2005/0228270 | A1 | 10/2005 | Lloyd et al. |
| 2005/0228274 | A1 | 10/2005 | Boese et al. |
| 2005/0288576 | A1 | 12/2005 | Fegert et al. |
| 2006/0033679 | A1 | 2/2006 | Gunji |
| 2006/0058604 | A1 | 3/2006 | Avinash et al. |
| 2006/0100526 | A1 | 5/2006 | Yamamoto et al. |
| 2006/0122497 | A1 | 6/2006 | Glossop |
| 2006/0161059 | A1 | 7/2006 | Wilson |
| 2006/0211914 | A1 | 9/2006 | Hassler, Jr. et al. |
| 2006/0241397 | A1 | 10/2006 | Govari et al. |
| 2006/0264749 | A1 | 11/2006 | Weiner et al. |
| 2006/0271056 | A1 | 11/2006 | Terrill-Grisoni et al. |
| 2007/0034731 | A1 | 2/2007 | Falco |
| 2007/0070194 | A1 | 3/2007 | Abe |
| 2007/0106114 | A1 | 5/2007 | Sugimoto et al. |
| 2007/0111726 | A1 | 5/2007 | Lambert et al. |
| 2007/0135803 | A1 | 6/2007 | Belson |
| 2007/0167754 | A1 | 7/2007 | Okuno et al. |
| 2007/0182729 | A1 | 8/2007 | Klingenbeck-Regn et al. |
| 2007/0197896 | A1 | 8/2007 | Moll et al. |
| 2007/0287905 | A1 | 12/2007 | Klingenbeck-Regn |
| 2008/0009697 | A1 | 1/2008 | Haider et al. |
| 2008/0021317 | A1 * | 1/2008 | Sumanaweera ...... A61B 8/4218 600/437 |
| 2008/0071142 | A1 | 3/2008 | Gattani et al. |
| 2008/0077158 | A1 | 3/2008 | Haider et al. |
| 2008/0103509 | A1 | 5/2008 | Goldbach |
| 2008/0121703 | A1 | 5/2008 | Li et al. |
| 2008/0125720 | A1 * | 5/2008 | Kim ............ A61B 17/3415 604/177 |
| 2008/0132932 | A1 | 6/2008 | Hoeppner et al. |
| 2008/0139916 | A1 | 6/2008 | Maier et al. |
| 2008/0162074 | A1 | 7/2008 | Schneider |
| 2008/0204000 | A1 * | 8/2008 | Groszmann ............ A61B 90/36 324/202 |
| 2008/0218588 | A1 | 9/2008 | Stetten |
| 2008/0221442 | A1 | 9/2008 | Tolkowsky et al. |
| 2008/0228188 | A1 | 9/2008 | Birkbeck et al. |
| 2008/0228195 | A1 | 9/2008 | von Jako et al. |
| 2008/0255442 | A1 | 10/2008 | Ashby et al. |
| 2008/0262345 | A1 | 10/2008 | Fichtinger et al. |
| 2008/0275334 | A1 | 11/2008 | Berting |
| 2008/0287802 | A1 | 11/2008 | Li et al. |
| 2008/0294034 | A1 | 11/2008 | Krueger et al. |
| 2008/0319448 | A1 | 12/2008 | Lavallee et al. |
| 2009/0030428 | A1 | 1/2009 | Omori et al. |
| 2009/0068620 | A1 | 3/2009 | Knobel et al. |
| 2009/0069671 | A1 | 3/2009 | Anderson |
| 2009/0154293 | A1 | 6/2009 | Sengupta et al. |
| 2009/0192519 | A1 | 7/2009 | Omori |
| 2009/0228813 | A1 | 9/2009 | Sekiguchi |
| 2009/0234329 | A1 | 9/2009 | Inamoto et al. |
| 2009/0306499 | A1 | 12/2009 | Van Vorhis et al. |
| 2010/0019918 | A1 * | 1/2010 | Avital ............ A61B 18/02 340/686.4 |
| 2010/0121174 | A1 | 5/2010 | Osadchy et al. |
| 2010/0137707 | A1 | 6/2010 | Hunter et al. |
| 2010/0160771 | A1 | 6/2010 | Gielen et al. |
| 2010/0210939 | A1 | 8/2010 | Hartmann et al. |
| 2010/0220914 | A1 | 9/2010 | Iwase et al. |
| 2010/0228117 | A1 * | 9/2010 | Hartmann ............ A61B 5/06 600/424 |
| 2010/0229118 | A1 | 9/2010 | Dorn et al. |

(56) References Cited

U.S. PATENT DOCUMENTS

| | | | |
|---|---|---|---|
| 2010/0234724 A1* | 9/2010 | Jacobsen | A61B 34/20 600/424 |
| 2010/0249506 A1 | 9/2010 | Prisco | |
| 2010/0274188 A1 | 10/2010 | Chang et al. | |
| 2010/0307516 A1 | 12/2010 | Neubauer et al. | |
| 2010/0312247 A1 | 12/2010 | Tuma | |
| 2011/0015523 A1 | 1/2011 | Sabata | |
| 2011/0054449 A1 | 3/2011 | Tien et al. | |
| 2011/0060213 A1 | 3/2011 | Mire et al. | |
| 2011/0066029 A1 | 3/2011 | Lyu et al. | |
| 2011/0118557 A1 | 5/2011 | McKenna et al. | |
| 2011/0137156 A1 | 6/2011 | Razzaque et al. | |
| 2011/0178389 A1 | 7/2011 | Kumar et al. | |
| 2011/0270083 A1 | 11/2011 | Shen | |
| 2011/0288600 A1 | 11/2011 | Ritchey et al. | |
| 2011/0295329 A1 | 12/2011 | Fitz et al. | |
| 2011/0313414 A1 | 12/2011 | Liu et al. | |
| 2012/0007747 A1 | 1/2012 | Boike et al. | |
| 2012/0143050 A1 | 6/2012 | Heigl | |
| 2012/0157887 A1* | 6/2012 | Fanson | A61F 2/46 600/595 |
| 2012/0168587 A1 | 7/2012 | Karsak et al. | |
| 2012/0188352 A1 | 7/2012 | Wittenberg et al. | |
| 2013/0023730 A1 | 1/2013 | Kitamura et al. | |
| 2013/0060146 A1 | 3/2013 | Yang et al. | |
| 2013/0060278 A1 | 3/2013 | Bozung et al. | |
| 2014/0005555 A1 | 1/2014 | Tesar | |
| 2014/0051922 A1 | 2/2014 | Guthart et al. | |
| 2014/0148808 A1 | 5/2014 | Inkpen et al. | |
| 2014/0200621 A1 | 7/2014 | Malackowski et al. | |
| 2014/0275985 A1* | 9/2014 | Walker | A61B 5/062 606/130 |
| 2014/0275987 A1 | 9/2014 | Bzostek et al. | |
| 2014/0303489 A1 | 10/2014 | Meier et al. | |
| 2014/0317910 A1 | 10/2014 | Govari et al. | |
| 2015/0182297 A1 | 7/2015 | Sandhu et al. | |
| 2016/0100899 A1 | 4/2016 | Jinno et al. | |
| 2016/0175543 A1 | 6/2016 | Frankhouser et al. | |
| 2016/0213430 A1 | 7/2016 | Mucha | |
| 2016/0249986 A1 | 9/2016 | Kruger et al. | |
| 2016/0310041 A1 | 10/2016 | Jenkins et al. | |
| 2016/0331269 A1 | 11/2016 | Kruger et al. | |
| 2017/0028112 A1 | 2/2017 | Drontle et al. | |
| 2017/0196508 A1 | 7/2017 | Hunter | |
| 2017/0258526 A1 | 9/2017 | Lang | |
| 2017/0270678 A1 | 9/2017 | Masumoto | |
| 2018/0021092 A2 | 1/2018 | Tausch et al. | |
| 2018/0093087 A1 | 4/2018 | Beach | |
| 2018/0296811 A1 | 10/2018 | Chan et al. | |
| 2019/0015644 A1 | 1/2019 | Thomspon Smith et al. | |
| 2019/0038366 A1 | 2/2019 | Johnson et al. | |
| 2019/0099141 A1 | 4/2019 | Garlow et al. | |
| 2022/0020161 A1 | 1/2022 | Mucha et al. | |
| 2022/0047338 A1 | 2/2022 | Mucha et al. | |
| 2022/0104882 A1 | 4/2022 | Mucha | |
| 2022/0192759 A1 | 6/2022 | Desinger et al. | |
| 2022/0257322 A1 | 8/2022 | Krüger et al. | |
| 2022/0273398 A1 | 9/2022 | Norman et al. | |

FOREIGN PATENT DOCUMENTS

| | | |
|---|---|---|
| DE | 20220584 U1 | 4/2004 |
| DE | 102004058272 A1 | 6/2005 |
| DE | 202007004507 U1 | 6/2007 |
| DE | 102007059691 A1 | 7/2008 |
| EP | 0691663 A1 | 1/1996 |
| EP | 1080695 A1 | 3/2001 |
| EP | 1380266 A1 | 1/2004 |
| EP | 1523951 A2 | 4/2005 |
| EP | 1925265 B1 | 1/2010 |
| EP | 2186474 A1 | 5/2010 |
| EP | 2305115 A1 | 4/2011 |
| EP | 1278458 B1 | 7/2011 |
| EP | 3506278 A1 | 7/2019 |
| JP | 2004-529679 A | 9/2004 |
| JP | 2011036600 A | 2/2011 |
| WO | WO-9605768 A1 | 2/1996 |
| WO | WO-9729678 A2 | 8/1997 |
| WO | WO-9932033 A1 | 7/1999 |
| WO | WO-02076302 A2 | 10/2002 |
| WO | WO-2005039391 A2 | 5/2005 |
| WO | WO-2006095027 A1 | 9/2006 |
| WO | WO-2006122001 A2 | 11/2006 |
| WO | WO-2007011314 A2 | 1/2007 |
| WO | WO-2007017642 A1 | 2/2007 |
| WO | WO-2007115825 A1 | 10/2007 |
| WO | WO-2008030263 A1 | 3/2008 |
| WO | WO-2008076079 A1 | 6/2008 |
| WO | WO-2008095068 A1 | 8/2008 |
| WO | WO-2008110553 A2 | 9/2008 |
| WO | WO-2009150564 A3 | 4/2010 |
| WO | WO-2010054645 A2 | 5/2010 |
| WO | WO-2010054646 A3 | 7/2010 |
| WO | WO-2010076676 A1 | 7/2010 |
| WO | WO-2010123858 A2 | 10/2010 |
| WO | WO-2010133320 A1 | 11/2010 |
| WO | WO-2011081690 A1 | 7/2011 |
| WO | WO-2011134083 A1 | 11/2011 |
| WO | WO-2011148299 A1 | 12/2011 |
| WO | WO-2012056034 A1 | 5/2012 |
| WO | WO-2012109760 A1 | 8/2012 |
| WO | WO-2012150567 A1 | 11/2012 |
| WO | WO-2013010138 A2 | 1/2013 |
| WO | WO-2013013718 A1 | 1/2013 |
| WO | WO-2013072434 A1 | 5/2013 |
| WO | WO-2013109527 A1 | 7/2013 |
| WO | WO-2013144334 A1 | 10/2013 |
| WO | WO-2014184382 A1 | 11/2014 |
| WO | WO-2015085011 A1 | 6/2015 |
| WO | WO-2017100180 A1 | 6/2017 |
| WO | WO-2020221940 A1 | 11/2020 |
| WO | WO-2021048439 A1 | 3/2021 |

OTHER PUBLICATIONS

Anonymous, Configuration ZSY 11100000864: Result, Aug. 14, 2008, 1 page.
Anonymous, Configuration ZSY 11100000864: Result, Sep. 25, 2008, 1 page.
Anonymous, Endoscopic view of the brain, Figure 3, no date given, 1 page.
Anonymous: "Inertial navigation system", Wikipedia, Mar. 8, 2019 (Mar. 8, 2019), XP055599140.
Bockholt, et al., Augmented Reality for Enhancement of Endoscopic Interventions, Proceedings of the IEEE Virtual Reality, 2003, 5 pages.
Brain Lab AG, Acceptance Protocol LGS, Purchase order No. 4500239188, Dec. 11, 2008, 1 page.
Brain Lab AG, Bod de Livraison, Aug. 5, 2008, 2 pages.
Brain Lab AG, Clinical User Guide, Vector Vision cranial / ENT, Version 7.8, 2008, 594 pages.
Brain Lab AG, Curve Dual Navigation Station—Technical User Guide Revision 1.1, Dec. 31, 2017Retrieved from the Internet: https:// userguides.brainlab.corn/wp-content/uploads/2019/12/Curve-1.2-Tech n i ca 1-User-Guide-English-60915-69 EN-Rev .1.1. pdf.
Brain Lab AG, Lieferschein, Sep. 22, 2008, 2 pages.
Dang, et al., Robust methods for automatic image-to-world registration in cone-beam CT interventional guidance; Medical Physics, AIP; vol. 39, No. 10; Oct. 2012; pp. 6484-6498.
Devernay, et al., 3D Reconstruction of the Operating Field for Image Overlay in 3D-Endoscopic Surgery, Nov. 2001, 1 page.
Devernay, Toward Endoscopic Augmented Reality for Robotically Assisted Minimally Invasive Cardiac Surgery, Feb. 2001, 6 pages.
European Patent Office, European Extended Search Report for EP 19169312.6, Jul. 3, 2019, 12 pages.
European Patent Office, International Search Report and Written Opinion for International (PCT)Patent Application No. PCT/EP2012/072783, Feb. 13, 2013, 10 pages.

(56) References Cited

OTHER PUBLICATIONS

European Patent Office, International Search Report and Written Opinion for PCT/EP2010/002991,Sep. 6, 2010, 11 pages.
European Patent Office, International Search Report and Written Opinion for PCT/EP2010/003822,Sep. 10, 2010, 13 pages.
European Patent Office, International Search Report and Written Opinion for PCT/EP2011/003563,Nov. 14, 2014, 12 pages.
European Patent Office, International Search Report and Written Opinion for PCT/EP2011/069065, Dec. 23, 2011, 8 pages.
European Patent Office, International Search Report and Written Opinion for PCT/EP2013/056802, Jul. 12, 2013, 12 pages.
European Patent Office, International Search Report and Written Opinion for PCT/EP2014/065030,Oct. 8, 2014, 12 pages.
European Patent Office, International Search Report and Written Opinion for PCT/EP2014/068447, Feb. 5, 2015, 14 pages.
European Patent Office, International Search Report and Written Opinion for PCT/EP2014/072282, Jan. 27, 2015, 12 pages.
European Patent Office, International Search Report and Written Opinion for PCT/EP2015/058107,Oct. 22, 2015, 10 pages.
European Patent Office, International Search Report and Written Opinion for PCT/EP2020/059643, May 12, 2020, 14 pages.
European Patent Office, International Search Report and Written Opinion for PCT/EP2020/062086, Aug. 7, 2020, 10 pages.
Fleig, et al., Surface Reconstruction of the Surgical Field from Stereoscopic Microscope Views in Neurosurgery, International Congress Series 1230, 2001, pp. 268-274.
Hirai, et al., Image-Guided Neurosurgery System Integrating AR-Based Navigation and Open-MRI monitoring, Computer Aided Surgery, Mar. 2005, pp. 59-71, vol. 10, No. 2.
International Search Report mailed on Jan. 20, 2015, for PCT Application No. PCT/EP2014/073493, filed on Oct. 31, 2014, 3 pages.
Jain, Fundamentals of Digital Image Processing, Prentice-Hall Inc., 1989,4 pages.
Jing et al., Navigating System for Endoscopic Sinus Surgery Based on Augmented Reality, IEEE/ICME International Conference on Complex Medical Engineering, 2007, pp. 185-188.
Konishi et al., Augmented reality navigation system for endoscopic surgery based on three-dimensional ultrasound and computed tomography: Application to 20 clinical cases, International Congress Series 1281, 2005, pp. 537-542. This paper pertains to a medical navigation system which uses an endoscope augmented with 3-D ultrasound and CT scan.
Lapeer, et al., Image-enhanced Surgical Navigation for Endoscopic Sinus Surgery: Evaluating Calibration, Registration and Tracking, The International Journal of Medica Robotics and Computer Assisted Surgery,2008, pp. 32-45, Nol. 4.
Lee Seongpung et al: "A Simple and Accurate Camera-Sensor Calibration for Surgical Endoscopes and Microscopes", Sep. 14, 2014 (Sep. 14, 2014), International Conference on Computer Analysis of Images and Patterns. CAIP 2017: Computer Analysis of Images and Patterns.
Maintz et al. "A Survey of Medical Image Registration", Medical Image Analysis, 2(1): 1-36, Mar. 1998.
Maurer et al., Registration Of Head Volume Images Using Implantable Fiducial Markers, IEEE Transactions on Medical Imaging 16.4 (1997): 447-462.
Mourgues, et al., 3D Reconstruction of the Operating Field for Image Overlay in 3D-Endoscopic Surgery, Proceedings IEEE and ACM International Symposium on Augmented Reality, Oct. 29-30, 2001, 1 page.
Mucha et al., Plausibility check for error compensation in electromagnetic navigation in endoscopic sinus surgery, Int. J. of Computer Assisted Radiology and Surgery (CARS), 2006, pp. 316-318.
Non-Final Office Action for U.S. Appl. No. 15/033,146 dated Mar. 10, 2022 , 6 pages.
Office action for U.S. Appl. No. 17/492,057, dated Mar. 9, 2022 8 pages.
Olwal, et al., Design and Evaluation of Interaction Technology for Medical Team Meetings; Interact 2011, Part 1; FIP International Federation for Information Processing 2011; 2011; pp. 505-522.
Olwal, et al., HybridSurface: Multi-user, multi-device, remote collaboration; Vimeo; https://vimeo.com/30581634; 2009; screen shots of video at five second intervals; entire video_.
Paul, et al., Augmented Virtuality Based on Stereoscopic Reconstruction in MultimodalImage-GuidedNeurosurgery: Methods and Performance Evaluation, Methods and Performance Evaluation, IEEE Transactions on Medical Imaging, 2005, pp. 1500-1511, vol. 24.
Pflugi Silvio et al: "Augmented marker tracking for peri-acetabular osteotomy surgery", 2017 39th Annual International Conference of the IEEE Engineering in Medicine and Biology Society (EMBC), IEEE, Jul. 11, 2017 (Jul. 11, 2017), pp. 937-941, XP033152153.
Rogalla, et al., Virtual Endoscopy and Related 3D Techniques, Medical Radiology Diagnostic Imaging,2001, 8 pages.
Sielhorst, et al., Advanced Medical Displays: A Literature Review of Augmented Reality, Journal of Display Technology, Dec. 2008, pp. 451-467, vol. 4, No. 4.
The International Bureau of WIPO, International Preliminary Report onPatentability for PCT/EP2020/062086, Nov. 2, 2021, 7 pages.
The International Bureau of WIPO, International Preliminary Report onPatentability for PCT/EP2020/062349, Nov. 2, 2021, 9 pages.
Thormahlen, Professor of Philips-Universitat Marburg biography, retrieved on Oct. 8, 2019, 9 pages.
Thormahlen, Three-Dimensional Endoscopy, Kluwer Academic Publishers, Dec. 2002, pp. 199-214.
Tsai R Y et al: "A New Technique for Fully Autonomous and Efficient 3D Robotics Hand/Eye Calibration", IEEE Transactions on Robotics and Automation, vol. 5, No. 3, Jun. 1, 1989 (Jun. 1, 1989), pp. 345-358, XP000028733.
United States Patent and Trademark Office, Final Office Action for U.S. Appl. No. 13/321,087, Oct. 21, 2015, 12 pages.
United States Patent and Trademark Office, Final Office Action for U.S. Appl. No. 13/321,087, Sep. 21, 2017, 18 pages.
United States Patent and Trademark Office, Final Office Action for U.S. Appl. No. 13/380,695, Jul. 16, 2014, 11 pages.
United States Patent and Trademark Office, Final Office Action for U.S. Appl. No. 13/380,695, Jul. 29, 2015, 5 pages.
United States Patent and Trademark Office, Final Office Action for U.S. Appl. No. 13/881,770, Nov. 20, 2015, 20 pages.
United States Patent and Trademark Office, Final Office Action for U.S. Appl. No. 14/358,108, Jan. 29, 2016, 12 pages.
United States Patent and Trademark Office, Final Office Action for U.S. Appl. No. 14/387,722, Dec. 28, 2018, 26 pages.
United States Patent and Trademark Office, Final Office Action for U.S. Appl. No. 14/387,722, Dec. 31, 2019, 23 pages.
United States Patent and Trademark Office, Final Office Action for U.S. Appl. No. 14/387,722, Jun. 30, 2021, 27 pages.
United States Patent and Trademark Office, Final Office Action for U.S. Appl. No. 14/890,480, Aug. 30, 2018, 22 pages.
United States Patent and Trademark Office, Final Office Action for U.S. Appl. No. 14/890,480, Aug. 4, 2017, 21 pages.
United States Patent and Trademark Office, Final Office Action for U.S. Appl. No. 14/903,381, Jul. 3, 2019, 20 pages.
United States Patent and Trademark Office, Final Office Action for U.S. Appl. No. 14/903,381, Jun. 20, 2018, 19 pages.
United States Patent and Trademark Office, Final Office Action for U.S. Appl. No. 14/903,381, Jun. 23, 2020, 17 pages.
United States Patent and Trademark Office, Final Office Action for U.S. Appl. No. 14/903,381, May 5, 2021, 21 pages.
United States Patent and Trademark Office, Final Office Action for U.S. Appl. No. 15/033,146, Apr. 16, 2020, 14 pages.
United States Patent and Trademark Office, Final Office Action for U.S. Appl. No. 15/033,146, Jul. 28, 2021, 21 pages.
United States Patent and Trademark Office, Final Office Action for U.S. Appl. No. 15/033,146, Mar. 7, 2019, 12 pages.
United States Patent and Trademark Office, Final Office Action for U.S. Appl. No. 15/303,793, Nov. 16, 2018, 33 pages.
United States Patent and Trademark Office, Final Office Action for U.S. Appl. No. 17/492,057, Dec. 9, 2021, 14 pages.

(56) References Cited

OTHER PUBLICATIONS

United States Patent and Trademark Office, Non-Final Office Action for U.S. Appl. No. 13/321,087, Apr. 22, 2015, 11 pages.
United States Patent and Trademark Office, Non-Final Office Action for U.S. Appl. No. 13/321,087, Dec. 9, 2016, 20 pages.
United States Patent and Trademark Office, Non-Final Office Action for U.S. Appl. No. 13/321,087, Jul. 13, 2018, 24 pages.
United States Patent and Trademark Office, Non-Final Office Action for U.S. Appl. No. 13/380,695, Dec. 4, 2013, 9 pages.
United States Patent and Trademark Office, Non-Final Office Action for U.S. Appl. No. 13/380,695, Dec. 9, 2014, 6 pages.
United States Patent and Trademark Office, Non-Final Office Action for U.S. Appl. No. 13/810,666, Dec. 18, 2015, 8 pages.
United States Patent and Trademark Office, Non-Final Office Action for U.S. Appl. No. 13/881,770, Jun. 18, 2015, 18 pages.
United States Patent and Trademark Office, Non-Final Office Action for U.S. Appl. No. 14/358,108, Jun. 12, 2015, 10 pages.
United States Patent and Trademark Office, Non-Final Office Action for U.S. Appl. No. 14/387,722, Apr. 13, 2018, 22 pages.
United States Patent and Trademark Office, Non-Final Office Action for U.S. Appl. No. 14/387,722, Aug. 25, 2017, 11 pages.
United States Patent and Trademark Office, Non-Final Office Action for U.S. Appl. No. 14/387,722, May 23, 2019, 24 pages.
United States Patent and Trademark Office, Non-Final Office Action for U.S. Appl. No. 14/890,480, Jan. 27, 2017, 20 pages.
United States Patent and Trademark Office, Non-Final Office Action for U.S. Appl. No. 14/890,480, Mar. 8, 2018, 20 pages.
United States Patent and Trademark Office, Non-Final Office Action for U.S. Appl. No. 14/903,381, Dec. 28, 2017, 18 pages.
United States Patent and Trademark Office, Non-Final Office Action for U.S. Appl. No. 14/903,381, Feb. 7, 2019, 21 pages.
United States Patent and Trademark Office, Non-Final Office Action for U.S. Appl. No. 14/903,381, Jan. 8, 2020, 17 pages.
United States Patent and Trademark Office, Non-Final Office Action for U.S. Appl. No. 14/903,381, Nov. 24, 2020, 17 pages.
United States Patent and Trademark Office, Non-Final Office Action for U.S. Appl. No. 15/033,146, Aug. 27, 2018, 16 pages.
United States Patent and Trademark Office, Non-Final Office Action for U.S. Appl. No. 15/033,146, Sep. 19, 2019, 15 pages.
United States Patent and Trademark Office, Non-Final Office Action for U.S. Appl. No. 15/033,146, Sep. 30, 2020, 13 pages.
United States Patent and Trademark Office, Non-Final Office Action for U.S. Appl. No. 15/303,793, Apr. 23, 2018, 31 pages.
United States Patent and Trademark Office, Non-Final Office Action for U.S. Appl. No. 15/303,793, Jun. 13, 2019, 52 pages.
United States Patent and Trademark Office, Non-Final Office Action in U.S. Appl. No. 17/374,865, mailed Oct. 13, 2022, 23 pages.
United States Patent and Trademark Office, Notice of Allowance for U.S. Appl. No. 13/321,087, Apr. 26, 2019, 5 pages.
United States Patent and Trademark Office, Notice of Allowance for U.S. Appl. No. 13/380,695, Feb. 17, 2016, 8 pages.
United States Patent and Trademark Office, Notice of Allowance for U.S. Appl. No. 13/810,666, Apr. 8, 2016, 5 pages.
United States Patent and Trademark Office, Notice of Allowance for U.S. Appl. No. 13/881,770, Jan. 20, 2017, 8 pages.
United States Patent and Trademark Office, Notice of Allowance for U.S. Appl. No. 14/358,108, Jun. 15, 2016, 8 pages.
United States Patent and Trademark Office, Notice of Allowance for U.S. Appl. No. 14/401,652, Sep. 1, 2015, 13 pages.
United States Patent and Trademark Office, Notice of Allowance for U.S. Appl. No. 14/890,480, Apr. 9, 2019, 8 pages.
United States Patent and Trademark Office, Notice of Allowance for U.S. Appl. No. 15/303,793, Oct. 18, 2019, 8 pages.
Von F. Hagenmuller, et al., Medical Imaging in Gastroenterology and Hepatology (Falk Symposium ,Band 124), [Book Description], 2 pages.
Von F. Hagenmuller, et al., Medical Imaging in Gastroenterology and Hepatology (Falk Symposium, D Band 124), Dec. 2002, 3 pages.
Von F. Hagenmuller, et al., Medical Imaging in Gastroenterology and Hepatology, Kluwer Academic Publishers, 2002, 3 pages.

* cited by examiner

FIG. 3

DEVICE AND METHOD FOR CONNECTING A MEDICAL INSTRUMENT TO A POSITION-DETECTING SYSTEM

CROSS REFERENCE TO RELATED APPLICATIONS

This application is the U.S. National Stage of International Application Number PCT/EP2014/065030 filed on Jul. 14, 2014 which application claims priority under 35 USC § 119 to German Patent Application No. 102013214067.3 filed on Jul. 17, 2013, which applications are hereby incorporated by reference in their entirety.

TECHNICAL FIELD

The invention relates to a device for connecting a medical instrument, in particular a medical instrument for invasive surgical interventions, to a location-detecting system, the medical instrument having an instrument shaft, an instrument tip and a working point.

BACKGROUND OF THE INVENTION

In this context, a location-detecting system is intended to mean a system which delivers location information to a medical instrument. The location information is useful in order to use an instrument in combination with imaging devices such as tomographs or tomographically obtained image data. In this context, location information is intended to mean the position and the orientation of the medical instrument in relation to a reference coordinate system. A reference coordinate system is a coordinate system of a location-detecting device or of a location-detecting system. The location information may be acquired by means of a location-detecting device with a corresponding measuring system.

During the conduct of invasive surgical interventions, preoperatively obtained image data of the patient, for example computed tomography recordings, are often used as planning data. Furthermore, it is usual to record images of the patient intraoperatively, i.e. with an endoscope, and to represent these together with the preoperatively compiled data on a monitor, respectively as an individual image or overlaid. In this way, for example, tissue to be removed or nerve paths or vessels lying in the operation region and potentially at risk from the surgical intervention can be made more clearly visible to the surgeon. This representation of the image data can therefore assist the surgeon to use the medical apparatus employed during the operation as efficiently as possible and with the least possible damage to the patient's surrounding tissue. In this case, the surgeon must first navigate the medical instrument as accurately as possible along a determined path into a usually preoperatively established intervention region in the patient's body and carry out the operative measures, for example the removal of tissue parts, as precisely as possible in the intervention region. Following the operative measures, the medical instrument must be navigated back out of the patient's body while being monitored. Therefore, invasive surgical interventions often require a high degree of accuracy of the location information of medical instruments which is being ascertained.

Furthermore, the mental correlation between the image data provided and the control of the medical instruments can easily lead to orientation problems for the surgeon and therefore to operational mistakes and/or lengthening of the operation.

For this reason, position-detecting or location-detecting systems are regularly used as an orientation aid for the surgeon during the operation, for example in order to assist navigation of medical instruments, in particular surgical instruments. During the operation, such systems record the coordinate transformation between the patient and at least one medical instrument. In many location-detecting systems, location information of a multiplicity of different medical instruments can be determined. The location information obtained is generally visualized on a monitor together with the preoperative planning data and/or the intraoperative image data. To this end, Localization elements, the location information of which is recorded by a measuring system as a location-detecting device, are arranged at particular positions of the patient as well as on the medical instruments.

In this way, the location information of the localization elements in the location-detecting system can initially be determined.

Such location-detecting systems may for example comprise optical, ultrasound-assisted or electromagnetic localization elements. For example, electromagnetic location-detecting systems which have a field generator are known. The field generator generates a generally alternating AC electric field in an operation region. Localization elements which have coils are arranged on a medical instrument to be navigated in this operation region. The AC electromagnetic field induces in these coils characteristic currents as a function of the orientation of the respective coil relative to the AC electromagnetic field, and the location information of the coils can be determined from these currents.

It is furthermore known to provide various medical instruments, for example pointer instruments, siphons, forceps, needles, scalpels, electrotomes, cauterizers, etc., with localization elements for determining the location information for such a location-detecting system and to register the respective medical instrument in the location-detecting system. During the registration of the medical instrument, the location of a reference—usually the working point of the instrument tip—relative to the localization element arranged on the medical instrument is calibrated and transmitted to the location-detecting system. The location of the reference point and orientation of the medical instrument in the coordinate system of the location-detecting system are therefore known and can be represented on the monitor together with the existing image data.

A requirement for registration of a medical instrument in a location-detecting system is that the medical instrument has at least one localization element. However, there are many medical instruments which do not have such a localization element and cannot therefore be used in a location-detecting system.

SUMMARY OF THE INVENTION

It is therefore an object of the present invention to provide a device for connecting a medical instrument to a location-detecting system, so that medical instruments which do not have their own localization element can be registered in a location-detecting system, in order that location information of the respective medical instrument can be determined by the location-detecting system and, for example, can be represented on a monitor.

According to the invention, the object is achieved by a device having a localization element for connecting a medical instrument to a location-detecting system, the medical instrument having an instrument shaft, an instrument tip and a working point. At least one localization element for determining location information, for instance orientation and position, of the device relative to a reference point can be arranged on the device. The device furthermore has a holding means for fastening to the medical instrument.

Preferably, the holding means has an instrument holder, at least a subsection of the medical instrument being engageable with the instrument holder and being fastenable to the instrument holder by at least one fixing means. The instrument holder may be for example, configured in the shape of a cup or a cylinder. Preferably, the instrument holder is configured in order to hold a subregion of the medical instrument. Furthermore, the instrument holder can preferably be fitted onto the medical instrument on the instrument tip side, i.e. the distal end of the medical instrument, and can be displaced along an instrument longitudinal axis on the instrument. Preferably, the instrument holder is fastened to the instrument shaft by the fixing means.

Preferably, the fixing means comprises a screw. The screw can for example be screwed into the device so that, as a result, its preferably flattened screw tip presses against an instrument shaft section which the instrument holder comprises, so as to hold the medical instrument in the instrument holder.

In a preferred embodiment of the invention, the fixing means has a clamping device, in order to hold the medical instrument in the instrument holder. The clamping device may for example have clamping jaws, which are to be clamped to the medical instrument by means of a screw mechanism.

Preferably, the device has a sensor holder which can hold the localization element. In this case, both embodiments in which the localization element is to be held reversibly and embodiments in which the localization element is to be held irreversibly in the sensor holder are provided.

In a preferred embodiment of the invention, the sensor holder and the localization element have guide means, by means of which the sensor element and localization element can be connected to one another, or engaged with one another, in such a way that the sensor holder and the localization element can be displaced relative to one another on a guide path. In this case, for example, the sensor holder may have a rail-shaped part and the localization element may have a corresponding carriage-shaped part. As an alternative the sensor holder may have a carriage-shaped part and the localization element may have a rail-shaped part.

Preferably, the guide means of the sensor holder and/or of the localization element are configured in such a way that a relative movement of the sensor holder and the localization element is possible only as far as a defined point on the guide path. To this end, at least a part of the guide path may, for example, have a tooth or a stop.

Preferably, the guide means of the sensor holder and/or of the localization element have a retaining means with a spring element, the localization element being fixable in a predefined position on the guide path by the retaining means. The retaining means is preferably configured to trigger the fixing by the movement of the localization element along the guide path. To this end, the rail-shaped part of the guide means may for example have a groove, and the carriage-shaped part of the guide means may have a resiliently held wedge, which can be tilted by the spring force into the groove of the rail-shaped part and therefore cause the fixing.

In a preferred embodiment of the invention the localization element is arranged firmly on the holding means. Removal of the localization element from the holding means is not provided in this embodiment.

Preferably, the device has an outer surface with an essentially cylindrical shape. The outer surface may, however, also be configured with an essentially cuboid or quadrilateral shape.

In an advantageous configuration of the invention, the device is configured in order to be connected to a control unit of the location-detecting system by a cable, in order to transmit signals from the localization element to the control unit of the location-detecting system. To this end, the device may have a cable or a connection for a cable, for example a jack socket. As an alternative, the device may send the signals of the localization element to the control unit of the location-detecting system via a radio device. In such a wireless embodiment, the device preferably has means for providing a supply current, for example an accumulator or battery.

Preferably, the holding means has a channel extending in the longitudinal direction of the holding means. The channel is open at both end sides of the holding means, so that at least the instrument tip of the medical instrument can be passed through the channel.

Furthermore, preferably, the channel has an essentially oval cross section. The advantage of the oval cross section is, in particular, that the holding means can be displaced along a curved region of an instrument longitudinal axis of a flexurally stiff and curved instrument tip.

According to the invention, a localization element held on the medical instrument by the device can be calibrated to the working point of the medical instrument. This may, for example, be done by a method in which a reference point is approached with the working point of the instrument tip, and at the same time the location and orientation of the localization element held on the instrument are detected. When the reference point is reached, the localization element is therefore calibrated to the instrument tip. Preferably, at the moment when the working point of the instrument tip reaches the reference point, the working point is automatically calibrated. This is, for example, made possible by a pressure sensor at the reference point, or an electrical circuit which is closed by contact of the working point of the instrument tip with the reference point. As an alternative or in addition, the method may provide that, as a starting condition for calibration of the localization element to the instrument tip, a check is made whether the reference point to be approached lies within a search sector which relates to the localization element held/to be held on the medical instrument. The search sector may be differently specifiable depending on the instrument. Preferably, the search sector is configured in the shape of a wedge. The wedge axis lies, in particular, coaxially with a longitudinal axis of the instrument tip and/or coaxially with a channel of the holding means, intended for the instrument to be passed through. The wedge tip preferably points toward and/or preferably lies at the center of the localization element. Preferably, the search sector is specified in such a way that an instrument tip lies inside the search sector when the localization element is held on the medical instrument.

As an alternative (or in addition), the device may also be configured in such a way that automatic calibration is carried out when the working point (i.e. for example the instrument tip) remains at the reference point for a predetermined time.

After successful calibration, the location data of the working point of the instrument tip may be determined by the location-detecting system by means of the location information provided by the respective localization element.

Particularly preferably, the reference point is arranged on a localization element which is connected to the location-detecting system and is registered. The localization element may likewise be the localization element of an instrument, so that two medical instruments can easily be registered at the same time within the location-detecting system. The exact position of the reference point within the location-detecting system can therefore be determined easily. The reference point arranged on the localization element is suitable for calibrating a new instrument, equipped with a further localization element, to the working point of the instrument. Such a calibration process may therefore also be carried out intraoperatively. A further or alternative reference point may be a localization element which is arranged on the patient and is configured for determining the location information of the patient within the location-detecting system.

It is particularly preferred for the reference point to be configured as a depression or an elevation (for example on a second instrument), in order to allow self-centering of a corresponding medical instrument at the reference point. A depression-shaped reference point is particularly suitable for self-centering of an instrument having a tip-shaped instrument tip with the reference point, since the instrument tip can be introduced into the depression and therefore guided along an inner surface of the depression to the midpoint thereof. Furthermore, preferably, the midpoint of the depression has a further local indentation with a smaller depression radius, into which an instrument tip can be introduced. The approaching of the depression midpoint with the instrument tip is therefore further facilitated. A reference point configured as an elevation is particularly suitable for the calibration of instruments which comprise a tubular instrument tip having an inner channel, for example siphons.

Preferably, the localization element has a sensor coil. Sensor coils are suitable for use in position-detecting systems having an AC electromagnetic field generated by a field generator.

Particularly preferably, the location-detecting system is configured in order to register and simultaneously manage a plurality of localization elements. The location information of a plurality of medical instruments equipped with localization elements can therefore simultaneously be determined as well as graphically and/or digitally represented. The management of a plurality of localization elements may, for example, be carried out by means of multiplexing. In the case of multiplexing, the registered localization elements are driven at a predetermined clock rate so that only one particular localization element is respectively driven by the location-detecting system at one time. In this case, it is advantageous that the location-detecting system can discriminate between active and inactive instruments. Inactive instruments may therefore be blocked out by the location-detecting system, for example by a corresponding filter, or the corresponding localization elements may be deactivated in order to increase the stability of the signals of the localization elements of the active instruments.

To this end, the multiplexer may, for example, be configured so that initially all the localization elements are activated and driven at the predetermined clock rate. As soon as a localization element of an instrument arranged in an operation region is detected, the remaining localization elements are deactivated or the corresponding instruments are blocked out until the active instrument leaves the operation region again. For the residence time of the active instrument in the Operation region, the corresponding localization element is preferably detected continuously by the location-detecting system. The location-detecting system may preferably be configured manually in order to detect a larger number than one instrument, for example two, simultaneously in the operation region by means of multiplexing, and only to deactivate the remaining localization elements or block out the corresponding instruments when this predetermined number of active instruments arranged in the operation region is reached.

In an alternative configuration of the invention, a device may be provided in order to unblock a particular instrument manually and/or activate the respective localization element. This may, for example, be done by means of a pressure sensor arranged on the instrument handle, which automatically detects when the instrument is being held in the hand. The control may be configured in such a way that the corresponding instrument remains active and unblocked until another instrument is activated, or unblocked. The system may be configured in order to manage a plurality of active instruments simultaneously. Furthermore, the system may be configured in order not to automatically deactivate or block out an activated instrument arranged in the operation region. This ensures that an instrument, for example, remains active for at least as long as it is arranged inside the operation region.

As an alternative, the instrument rack may, for example, be configured in order to detect inactive instruments which are placed on an instrument rack and forward this information to the location-detecting system, so that the location-detecting system deactivates or blocks out these inactive instruments.

BRIEF DESCRIPTION OF THE DRAWINGS

The invention will now be explained in more detail with the aid of an exemplary embodiment with reference to the figures. In the figures.

DETAILED DESCRIPTION

Figure 1:
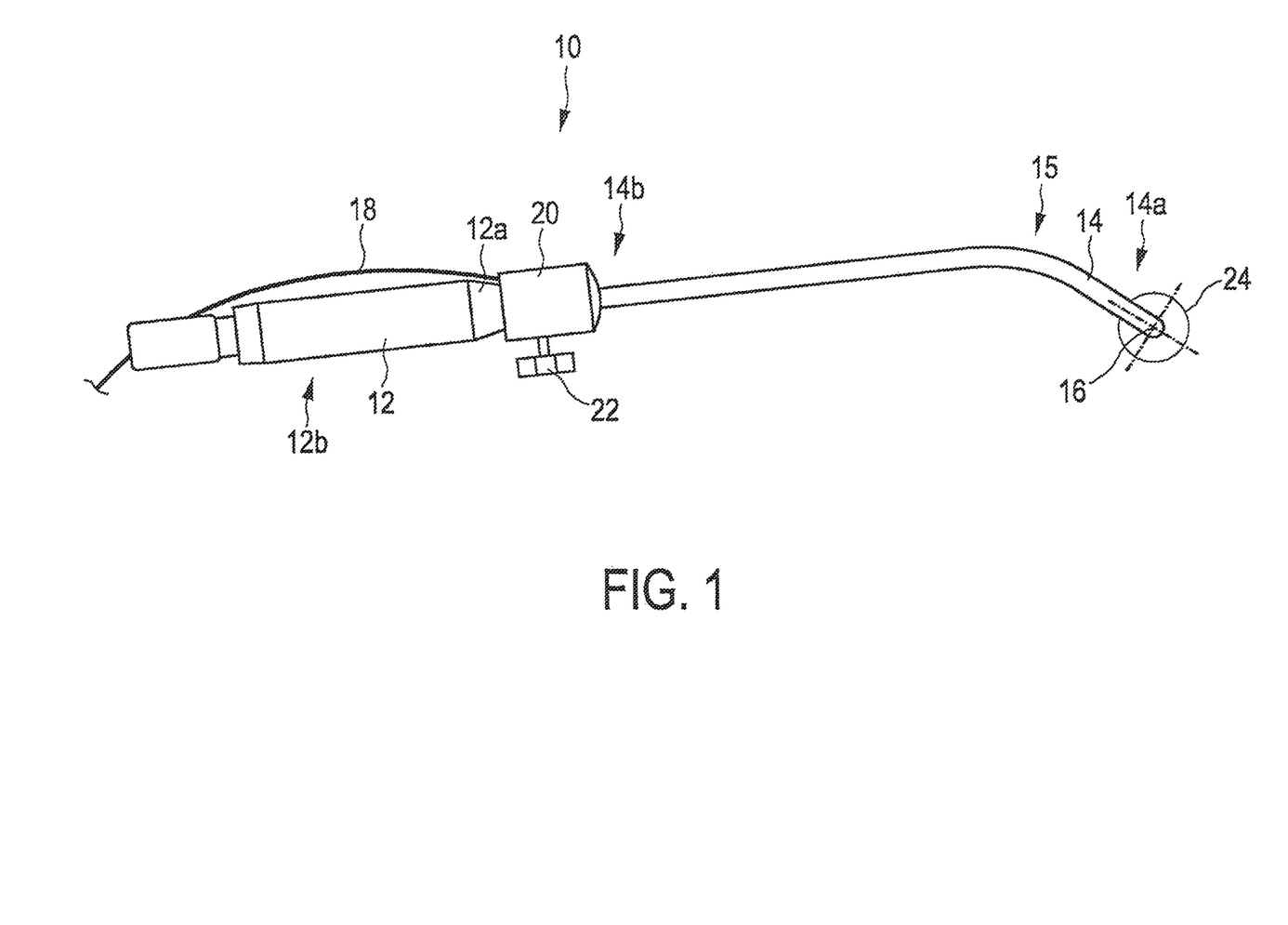
FIG. 1 shows a schematic side view of a medical instrument with localization element fitted thereon.

The medical instrument 10 represented in FIG. 1 has an instrument shaft 12 and an instrument tip 14. The instrument shaft 12 has a distal shaft region 12a and a handle region 12b, a proximal tip region 14b of the instrument tip 14 being arranged on the distal shaft region 12a. The instrument shaft 12 may be configured in one piece or in several pieces, separately, with the instrument tip 14.

The instrument tip 14 has a distal tip region 14a, on the end of which facing away from the proximal tip region 14b a working point 16 is arranged. The instrument tip 14 furthermore has a curved region 15, which is next to the distal tip region 14a. In alternative embodiments, the instrument tip 14 may also have curvatures stronger (smaller radius) than represented, or further curvatures. The instrument shaft 12 and the instrument tip 14 have an essentially round cross section.

A localization element 20 is arranged next to the distal shaft region 12*a* on the proximal tip region 14*b* of the instrument tip 14. According to the embodiment shown, the distal shaft region 12*a* has a conical taper extending in the direction of the instrument tip 14, which can be engaged at least partially with the localization element 20. The localization element 20 is secured against displacement along a longitudinal axis of the instrument tip 14 by means of a clamping screw 22 on the proximal tip region of the instrument tip. Furthermore, the localization element 20 has a cable 18 for connection to a control unit 26 shown in FIG. 3.

By means of a reference point 24, the localization element 20 can be calibrated to the working point 16 of the medical instrument 10 for calibration. The calibration process may be carried out essentially automatically by the operator bringing the working point 16 of the medical instrument 10 into contact with the reference point 24 and, for example, maintaining this state for a predetermined time—for example from 1 to 2 seconds. As an alternative, for example, the reference point 24 may have a sensor (not represented here) which detects the moment of contact of the working point 16 with the reference point 24 and forwarding a corresponding signal to the control unit 26, so that the control unit 26 can record the location data of the localization element 20 at the time of contact of the working point 16 with the reference point 24 and therefore complete the calibration measurement. After calibration has been carried out, the location information of the working point 16 of the medical instrument in an operation region can be determined by means of the sensor signals transmitted from the localization element 20 to the location-detecting system.

Figure 2:
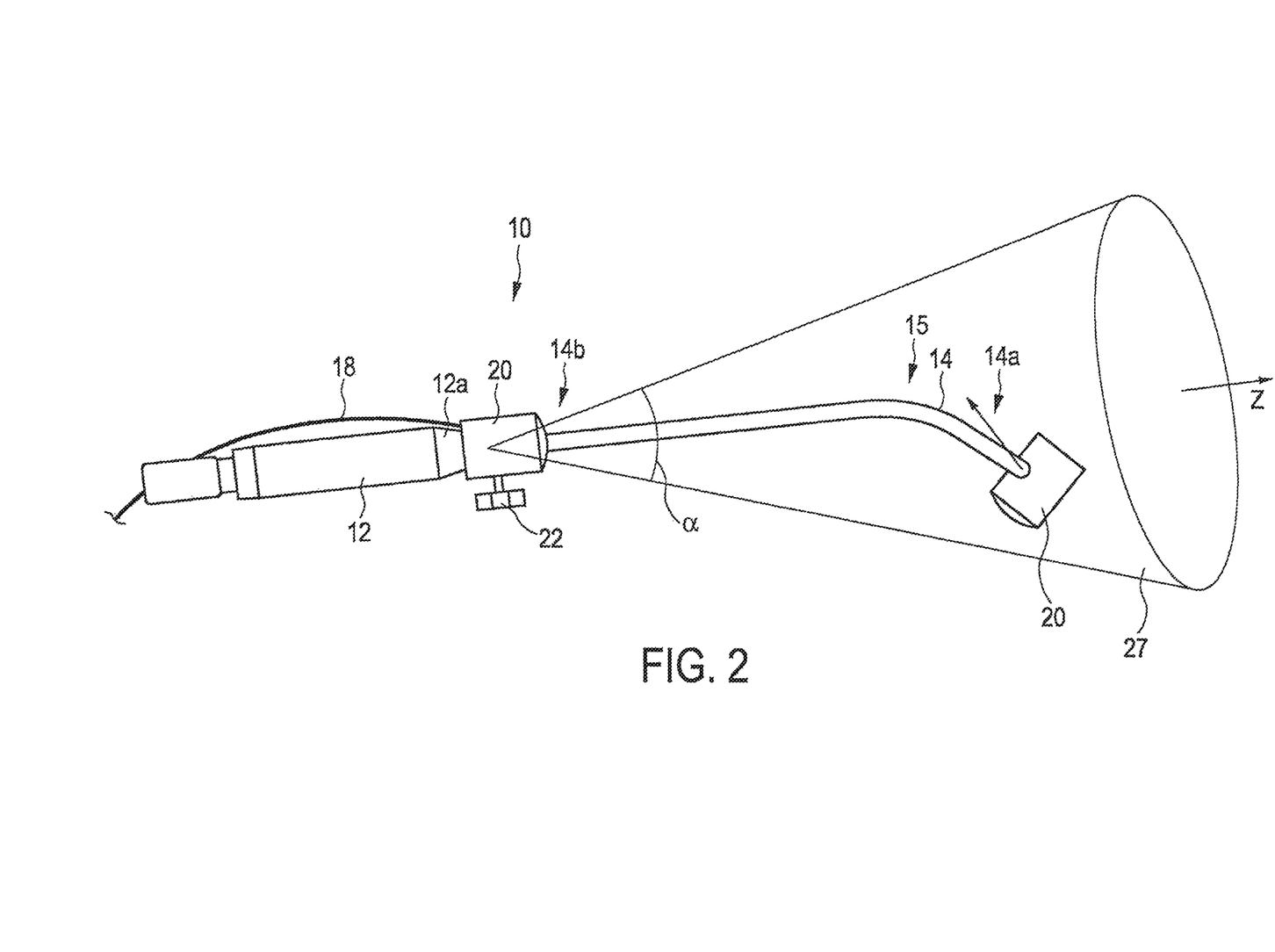
FIG. 2 shows the view of the medical instrument of FIG. 1, a further localization element being arranged on the instrument tip.

As shown by FIG. 2, a plurality of localization elements 20 may be arranged according to the invention on a medical instrument 10, One localization element 20 is already arranged in this view on the proximal tip region 14*b* of the instrument tip 14 as previously in FIG. 1, while a further localization element 20 is furthermore held on the distal tip region 14*a* and can be displaced toward the proximal tip region 14*b* along the tip longitudinal axis. The advantage of using a plurality of localization elements 20 on a medical instrument 10 is that the localization elements 20 provide mutually complementary and partially redundant location information, and measurement variations or measurement errors can therefore be detected by the control unit 26 of the location-detecting system.

Likewise shown in FIG. 2 is a wedge-shaped search sector 27. The search sector 27 relates to the localization element 20 held on the medical instrument 10 in the proximal tip region 14*b*. The wedge axis z lies coaxially with the longitudinal axis of the instrument tip 14. The wedge tip of the wedge-shaped search sector 27 points toward and lies at the center of the localization element 20 which is held in the proximal tip region 14*b*. The wedge-shaped search sector 27 therefore starts from the localization element 20 and extends and widens in the distal direction. Preferably, it ends at a defined distance from the localization element 20 and therefore defines a search space delimited on all sides. The search sector 27 is in the present case specified in such a way that an instrument tip 14 lies inside the search sector 27 when the localization element 20 is held on the medical instrument 10. The search sector 27 may also have a different shape, and need not be wedge-shaped. The purpose of the search sector 27 is to trigger automatic calibration only when it is found that the position data of the reference point 24, detected by the location-detecting system, lie inside the position data space (set of position data falling within the search sector) spanned by the search sector 27. In embodiments of the medical instrument 10 with an instrument shaft 12 and instrument tip 14 which can be separated from one another, the localization element 20 may be configured in order to be fitted directly onto the proximal tip region 14*b* when the instrument shaft 12 and the instrument tip 14 are separated from one another. After the fitting of the localization element 20, the instrument shaft 12 and the instrument tip 14 may be reconnected to one another.

As an alternative, embodiments are provided in which the localization element 20 can be fitted onto the instrument shaft 12. To this end, in principle, the same holding means as for fastening to the instrument tip 14 are suitable, the dimensions of the instrument shaft 12 needing to be taken into account.

Figure 3:
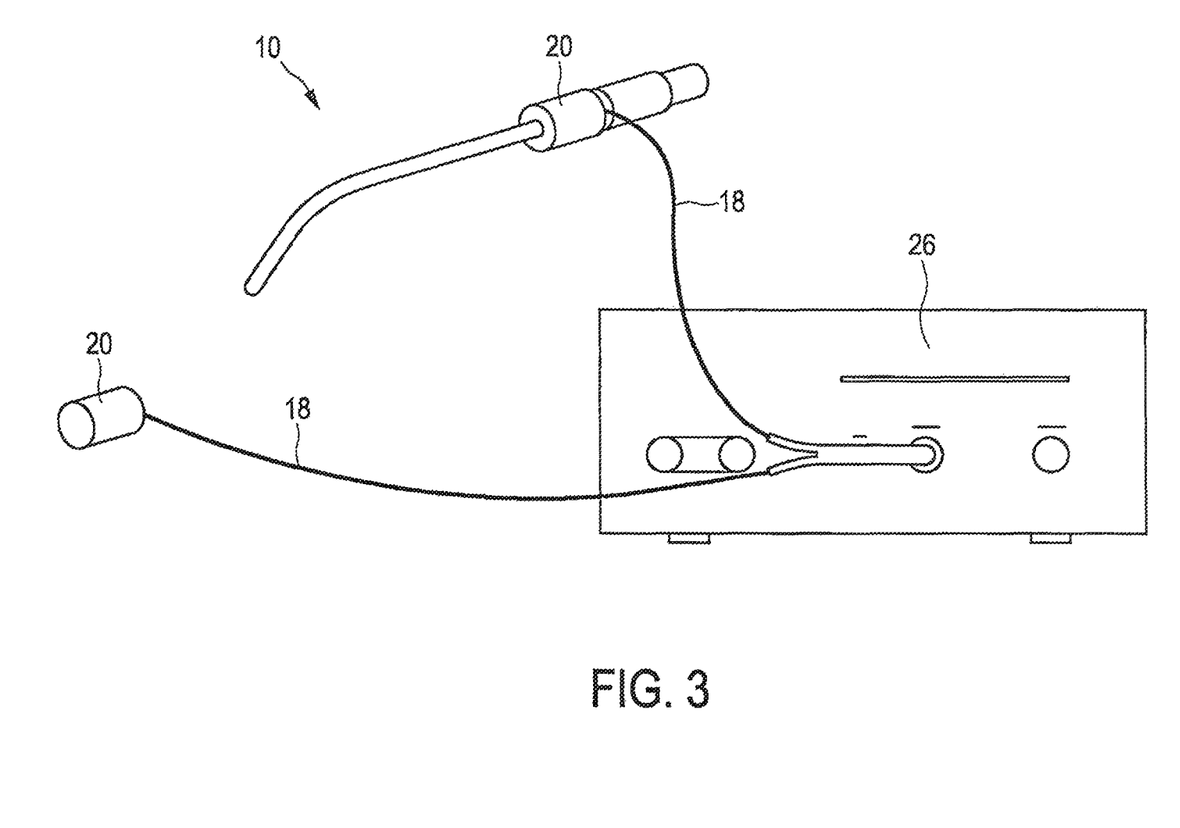
FIG. 3 shows a front view of a control unit with localization element coupled thereto, a localization element being arranged on a medical instrument.

According to the invention, a control unit 26 (as represented in FIG. 3) may be connected to a plurality of localization elements 20, preferably in each case by a cable 18. In this case, one or more localization elements 20 may respectively be arranged on a medical instrument 10. Furthermore, the localization elements 20 may be arranged on different medical instruments 10, only one medical instrument 10 being shown in FIG. 3. The control unit 26 may have a filter in order to block out inactive instruments 10, which are arranged for example on an instrument rack (not represented). In this way, the stability of the signals of the active instruments 10 is increased.

LIST OF REFERENCES

10 medical instrument
12 instrument shaft
12*a* distal shaft region
12*b* handle region
14 instrument tip
14*a* distal tip region
14*b* proximal tip region
15 curved region
16 working point
18 cable
20 localization element
22 clamping screw
24 reference point.
26 control unit
27 search sector
z cone axis

The invention claimed is:

1. A location-detecting system for determining location information of a medical instrument intraoperatively, the location-detecting system comprising:
   a reference point, wherein a location of the reference point within a coordinate system of the location-detecting system is determinable; and
   an instrument tracking device comprising at least one holding means for fastening the instrument tracking device to the medical instrument so that the medical instrument is connected to the location-detecting system, wherein said medical instrument comprises an instrument shaft and an instrument tip having a working point, said instrument tracking device comprising at least one localization element arranged on the instrument tracking device that is configured for use with the reference point and working point, wherein said reference point and said working point are not the same, to calibrate the at least one localization element to the working point, the at least one localization element comprising a sensor coil; and a control unit for recording location data of the at least one localization element, wherein the instrument tracking device is connectable by a cable to the control unit so that the at least one localization element can transmit sensor signals representing said location data of the instrument tracking device and the medical instrument fastened thereto to the control unit, and wherein the location-detecting system is configured:

to detect location and orientation of the instrument tracking device within the coordinate system of the location-detecting system and to automatically calibrate said localization element of the instrument tracking device to the working point of said medical instrument when the location-detecting system detects that the reference point lies within a search sector of the at least one localization element of the instrument tracking device fastened to the medical instrument, wherein the search sector is configured in a wedge shape, wherein the wedge is aligned coaxially with a longitudinal axis of the instrument, or aligned coaxially with a channel of the holding means, or both.

2. The location-detecting system according to claim 1, wherein the at least one holding means comprises an instrument holder, wherein at least a subsection of the medical instrument is engageable with the instrument holder and is fastenable to the instrument holder by at least one fixing means of the instrument tracking device.

3. The location-detecting system according to claim 2, wherein the fixing means comprises a screw, which is configured to be screwed into the instrument tracking device such that a flattened tip of the screw presses against a section of the instrument shaft thereby holding the medical instrument in the instrument holder.

4. The location-detecting system according to claim 2, wherein the fixing means comprises a clamping device.

5. The location-detecting system according to claim 1, wherein the instrument tracking device comprises a sensor holder configured to hold the localization element.

6. The location-detecting system according to claim 1, wherein the localization element is arranged irreleasably on the at least one holding means.

7. The location-detecting system according to claim 1, wherein the instrument tracking device comprises a cylindrical outer surface.

8. The location-detecting system according to claim 1, wherein the at least one holding means comprises a channel extending in a longitudinal direction, wherein the channel is open at both end sides of the at least one holding means, and wherein at least the instrument tip of the medical instrument is passable through the channel.

9. The location-detecting system according to claim 8, wherein the channel comprises an oval cross section.

10. A method for using the instrument tracking device of the location-detecting system according to claim 1, wherein the instrument tracking device is fastened to the medical instrument and wherein the at least one localization element is calibrated to the working point of the medical instrument, the method comprising: approaching a reference point with the working point of the instrument tip, and simultaneously detecting the location and orientation of the localization element held on the medical instrument, and wherein when the working point of the instrument tip reaches the reference point, the working point is automatically calibrated, or automatic calibration is carried out when the working point remains at the reference point for a predetermined time.

11. The location-detecting system according to claim 1, wherein the location-detecting system is configured to have as a starting condition for calibration of the localization element to the instrument tip to determine whether the reference point to be approached lies within the search sector.

12. The location-detecting system according to claim 1, wherein the reference point is formed to have a depression configured to receive and self-center a corresponding medical instrument.

13. The location-detecting system according to claim 12, wherein the depression further comprises a local indentation at a midpoint of the depression, wherein the local indentation has a radius smaller than the depression and is configured to receive an instrument tip.

14. The method according to claim 10, wherein the search sector wedge has a tip that points toward, lies at a center of the localization element, or both.

\* \* \* \* \*